(12) United States Patent
Hong et al.

(10) Patent No.: US 8,670,117 B2
(45) Date of Patent: Mar. 11, 2014

(54) INSPECTION APPARATUS

(75) Inventors: Jong-Kyu Hong, Gwangju-si (KR);
Monn-Young Jeon, Seoul (KR);
Hong-Min Kim, Seoul (KR); Jung Hur,
Bucheon-si (KR); Sang-Kyu Yun,
Chungju-si (KR)

(73) Assignee: Koh Young Technology Inc., Seoul (KR)

( * ) Notice: Subject to any disclaimer, the term of this patent is extended or adjusted under 35 U.S.C. 154(b) by 199 days.

(21) Appl. No.: 13/295,707

(22) Filed: Nov. 14, 2011

(65) Prior Publication Data
US 2012/0127463 A1    May 24, 2012

(30) Foreign Application Priority Data

Nov. 12, 2010 (KR) .................. 10-2010-0112764

(51) Int. Cl.
*G01N 21/88* (2006.01)

(52) U.S. Cl.
USPC .................... 356/237.5; 356/237.4

(58) Field of Classification Search
USPC .................. 356/237.1–237.5, 600–623; 382/141–151
See application file for complete search history.

(56) References Cited

U.S. PATENT DOCUMENTS

| | | | | |
|---|---|---|---|---|
| 5,229,835 A * | 7/1993 | Reinsch | ........................ | 356/600 |
| 5,311,018 A * | 5/1994 | Zana et al. | .................... | 250/330 |
| 5,559,338 A * | 9/1996 | Elliott et al. | ................ | 250/492.1 |
| 6,040,910 A * | 3/2000 | Wu et al. | ........................ | 356/613 |
| 6,362,877 B1 * | 3/2002 | Kobayashi et al. | ......... | 356/237.5 |
| 7,545,512 B2 * | 6/2009 | Kim et al. | ...................... | 356/514 |
| 2002/0014577 A1 * | 2/2002 | Ulrich et al. | ................... | 250/205 |
| 2004/0119971 A1 * | 6/2004 | Isozaki et al. | .............. | 356/237.2 |
| 2004/0160607 A1 | 8/2004 | Lin et al. | | |
| 2006/0007436 A1 * | 1/2006 | Kurosawa et al. | .......... | 356/237.4 |
| 2009/0051929 A1 * | 2/2009 | Koh et al. | ...................... | 356/602 |
| 2010/0302364 A1 * | 12/2010 | Kim et al. | ...................... | 348/136 |
| 2011/0001818 A1 * | 1/2011 | Hur et al. | ......................... | 348/87 |
| 2011/0002527 A1 * | 1/2011 | Jeong et al. | .................... | 382/141 |
| 2013/0215262 A1 * | 8/2013 | Jeong et al. | .................... | 348/126 |

FOREIGN PATENT DOCUMENTS

| | | |
|---|---|---|
| JP | 05-172756 | 7/1993 |
| JP | 6-72046 | 10/1994 |
| JP | 2000-012999 | 1/2000 |
| JP | 2004-158819 | 6/2004 |
| JP | 2006-030196 | 2/2006 |

(Continued)

*Primary Examiner* — Hoa Pham
(74) *Attorney, Agent, or Firm* — Kile Park Reed & Houtteman PLLC (57) ABSTRACT

An inspection apparatus includes a work stage part, an optical module, and an optical module moving part. The work stage part receives a board. The work stage part includes work stages disposed in parallel. The optical module includes a projecting part disposed over the board, an image capturing part disposed at a side portion of the projecting part to receive the grating pattern light and capture a reflection image, and an optical path changing part changing a path of the grating pattern light and guiding the grating pattern light to the image capturing part so that the grating pattern light is downwardly incident into the image capturing part. The optical module moving part is disposed over and coupled to the optical module to move the optical module. Thus, time may be reduced and a space may be secured, required for inspecting a board.

10 Claims, 5 Drawing Sheets

(56) References Cited

FOREIGN PATENT DOCUMENTS

| JP | 2007-318119 | 12/2007 |
|---|---|---|
| JP | 2009-092485 | 4/2009 |
| JP | 2010-078619 | 4/2010 |
| JP | 2010-107250 | 5/2010 |
| JP | 2010-151666 | 7/2010 |
| KR | 10-2010-0023992 | 3/2010 |

* cited by examiner

INSPECTION APPARATUS

CROSS REFERENCE TO RELATED APPLICATION

This application claims priority from and the benefit of Korean Patent Application No. 2010-112764 filed on Nov. 12, 2010, which is hereby incorporated by reference for all purposes as if fully set forth herein.

BACKGROUND OF THE INVENTION

1. Field of the Invention

Exemplary embodiments of the present invention relate to an inspection apparatus.

More particularly, exemplary embodiments of the present invention relate to an inspection apparatus that judges whether a measurement target formed on a board is good or bad.

2. Discussion of the Background

Generally, at least one printed circuit board (PCB) is employed in an electronic device, and various circuit elements such as a circuit pattern, a connection pad part, a driver chip electrically connected to the connection pad part, etc. are mounted on the PCB.

A board inspection apparatus is typically used to check whether the various circuit elements are formed or configured good or not on the printed circuit board.

In a conventional board inspection apparatus, considerable time and large workspace is required for inspecting a PCB.

Thus, an inspection apparatus is required capable of reducing time and securing a space, required for inspecting a PCB.

SUMMARY OF THE INVENTION

Exemplary embodiments of the present invention provide an inspection apparatus capable of reducing time and securing a space, required for inspecting a board.

Additional features of the invention will be set forth in the description which follows, and in part will be apparent from the description, or may be learned by practice of the invention.

An exemplary embodiment of the present invention discloses an inspection apparatus. The inspection apparatus includes a work stage part, an optical module, and an optical module moving part. The work stage part moves a board to a measurement location and supports the board. The optical module includes a projecting part disposed over the board to project grating pattern light to the board, an image capturing part disposed at a side portion of the projecting part to receive the grating pattern light upwardly reflected by the board and capture a reflection image, and a first optical path changing part changing a path of the grating pattern light upwardly reflected by the board and guiding the grating pattern light to the image capturing part so that the grating pattern light is downwardly incident into the image capturing part. The optical module moving part is disposed over the optical module and coupled to the optical module to move the optical module.

For example, the work stage part may include a target moving instrument moving the board to the measurement location. The target moving instrument may move the board in a first direction, and the optical module moving part may move the optical module in a second direction substantially perpendicular to the first direction. The image capturing part may be disposed at a first side portion of the projecting part corresponding to the second direction. The inspection apparatus may further include a cable guiding part disposed at a second side portion opposite to the first side portion of the projecting part at which the image capturing part is disposed. The optical module moving part may be disposed over and coupled to the cable guiding part over.

In an exemplary embodiment, the first optical path changing part may include a first mirror horizontally reflecting the grating pattern light that is upwardly reflected by the board toward the side portion of the projecting part at which the image capturing part is located. The first optical path changing part may further include a second mirror downwardly reflecting the grating pattern light that is horizontally reflected by the first mirror toward the image capturing part.

The projecting part may be disposed substantially perpendicular to the board, and the optical module may further include a second optical path changing part changing an optical path so that the grating pattern light from the projecting part is slantly incident onto the board. The optical module may include 2m projecting parts ('m' is a natural number), and the 2m projecting parts may be spaced at a regular interval on a circumference that is substantially parallel with the board when viewed in a plan view. The second optical path changing part may include a third mirror disposed under each of the projecting parts and a fourth mirror disposed under the third mirror. The third mirror reflects the grating pattern light that is downwardly incident onto the third mirror in a direction substantially perpendicular to the projecting part toward the fourth mirror disposed under and facing the projecting part, and the fourth mirror reflects the grating pattern light provided from the third mirror toward the board. Each of the 2m projecting parts may include a light source generating light and a grating element converting the light from the light source into grating pattern light, and the grating element corresponding to each of the 2m projecting parts is moved by one grating moving instrument.

The optical module may further include an illuminating part integrally coupled to the projecting part, the image capturing part and the first optical path changing part and disposed under a body of the optical module to provide light to the board.

Another exemplary embodiment of the present invention discloses an inspection apparatus. The inspection apparatus includes a target moving part moving a board to a measurement location, a projecting part projecting grating pattern light onto the board, an image capturing part disposed at a side portion of the projecting part to capture a reflection image by receiving the grating pattern light reflected by the board, and an optical path changing part changing a path of the grating pattern light reflected by the board and guiding the grating pattern light to the image capturing part.

In an exemplary embodiment, the inspection apparatus may further include at least two work stages disposed in parallel. Each work stage receives a board from an adjacent apparatus and supports the received board independently and an inspection for each board is independently performed.

In an exemplary embodiment, the inspection apparatus may further include an optical module moving part disposed over the projecting part and the image capturing part to move the projecting part and the image capturing part.

In an exemplary embodiment, the optical path changing part may include a first mirror horizontally reflecting the grating pattern light that is upwardly reflected by the board toward the side portion of the projecting part at which the image capturing part is located, and a second mirror downwardly reflecting the grating pattern light that is horizontally reflected by the first mirror toward the image capturing part.

Still another exemplary embodiment of the present invention discloses an inspection apparatus. The inspection apparatus includes a projecting part projecting grating pattern light to a board, an image capturing part receiving the grating pattern light reflected by the board and capturing a reflection image, an optical path changing part comprising at least one mirror changing an optical path so that the grating pattern light from the projecting part is slantly incident onto the board and a mirror fixing portion fixing the mirror, and an illuminating part coupled to the mirror fixing portion of the optical path changing part and disposed under the mirror fixing portion to provide light to the board.

In an exemplary embodiment, the inspection apparatus may include 2m projecting parts ('m' is a natural number), each of which may be disposed substantially perpendicular to the board, and the 2m projecting parts may be spaced at a regular interval on a circumference that is substantially parallel with the board when viewed in a plan view. The optical path changing part may include a third mirror disposed under each of the projecting parts and a fourth mirror disposed under the third mirror. The third mirror reflects the grating pattern light that is downwardly incident onto the third mirror in a direction substantially perpendicular to the projecting part toward the fourth mirror disposed under and facing the projecting part, and the fourth mirror reflects the grating pattern light provided from the third mirror toward the board.

In an exemplary embodiment, the inspection apparatus may further include a work stage part receiving the board from an adjacent apparatus and moving the board to a measurement location, the work stage part comprising at least two work stages disposed in parallel to support the board, and an optical module moving part disposed over the projecting part and the image capturing part and coupled to the projecting part and the image capturing part to move the projecting part and the image capturing part.

According to the present invention, the board inspection apparatus includes a plurality of work stages, and performs a board inspection independently for each work stage, to thereby greatly reduce time required for inspecting a board. In addition, an optical module moving part for moving an optical module including projecting parts is disposed over the optical module, and an image capturing part receiving grating pattern light generated from the projecting part is disposed at a side portion of the projecting part, to secure a space, which become small due to installing the work stages.

It is to be understood that both the foregoing general description and the following detailed description are exemplary and explanatory and are intended to provide further explanation of the invention as claimed.

BRIEF DESCRIPTION OF THE DRAWINGS is The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

Figure 1:
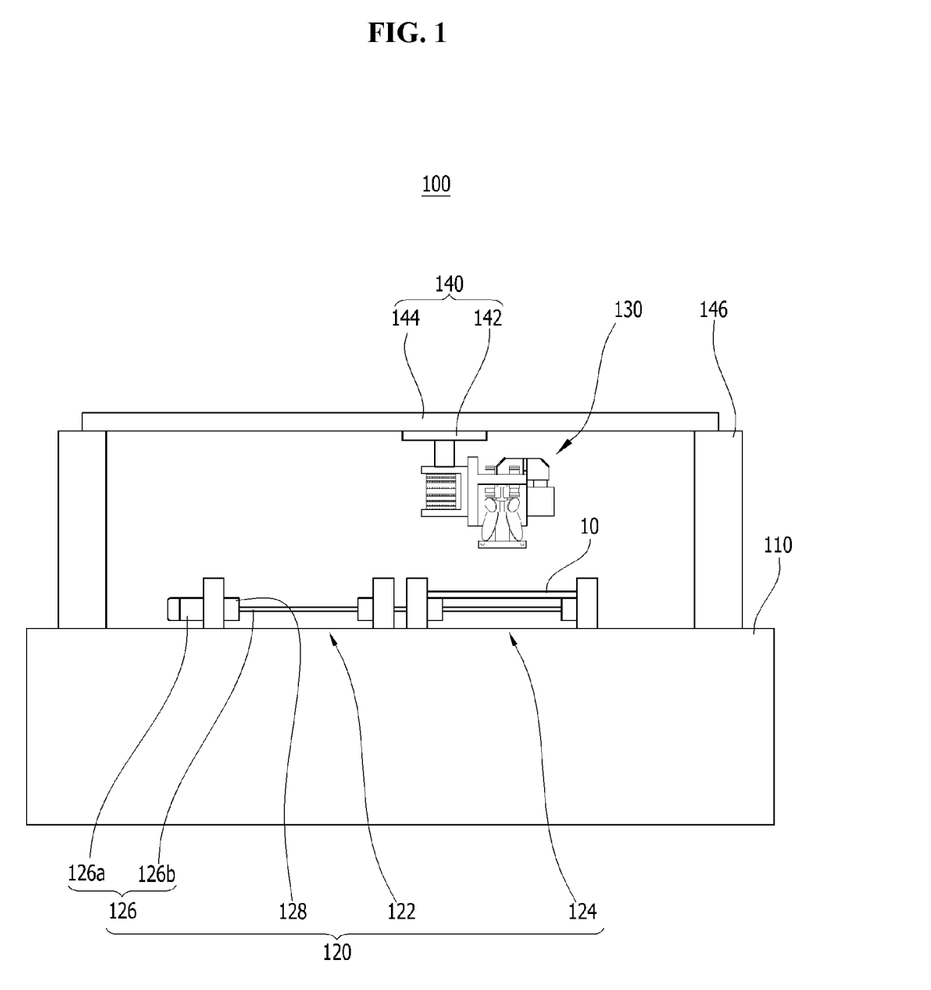
FIG. 1 is a front view illustrating a board inspection apparatus according to an exemplary embodiment of the present invention.
Figure 2:
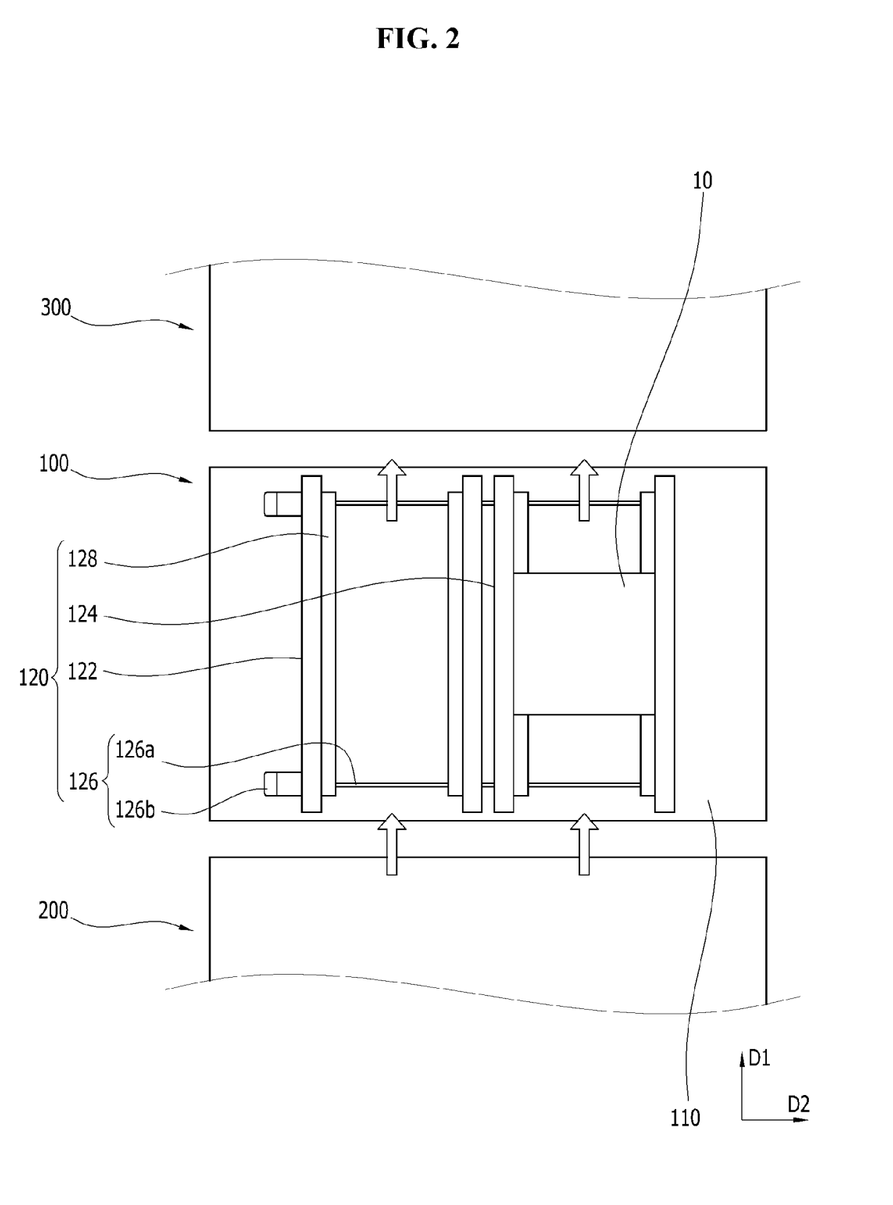
FIG. 2 is a plan view illustrating a work stage part of the board inspection apparatus illustrated in FIG. 1.
Figure 3:
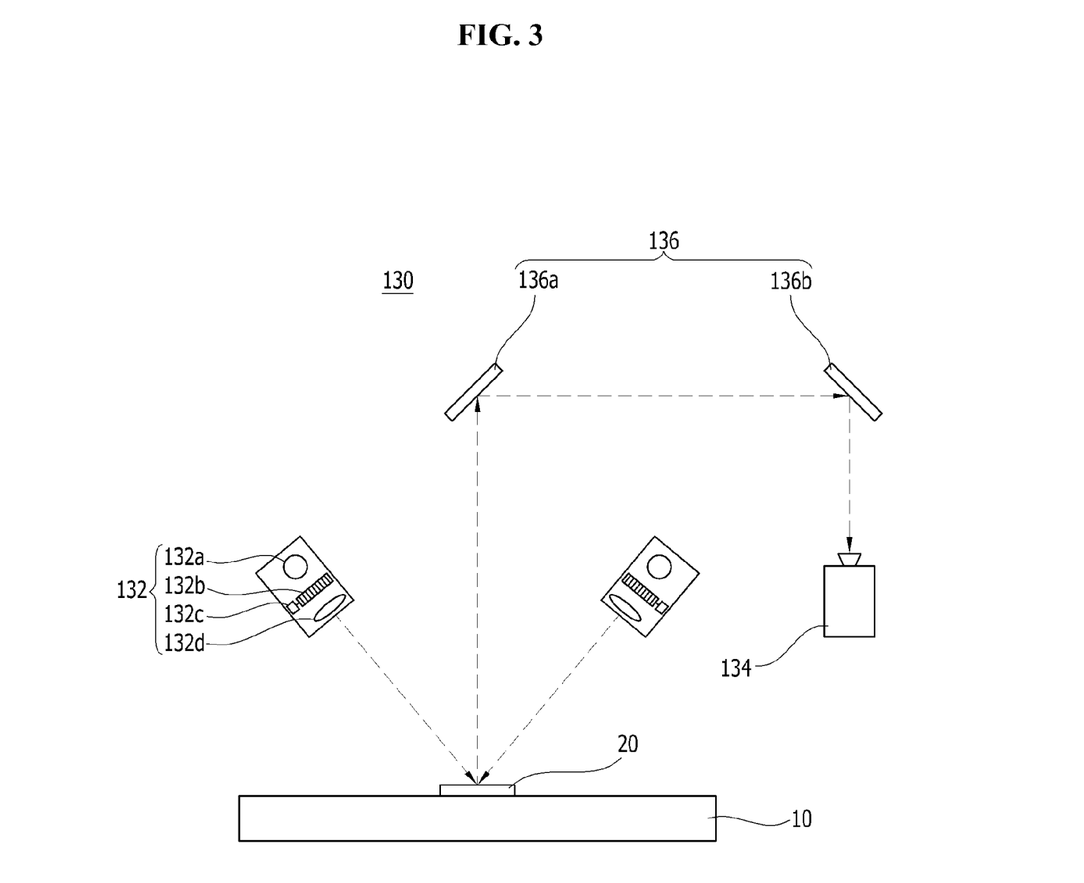
FIG. 3 is a conceptual view illustrating an optical path of an optical module of the board inspection apparatus illustrated in FIG. 1.

FIG. 1 is a front view illustrating a board inspection apparatus according to an exemplary embodiment of the present invention. FIG. 2 is a plan view illustrating a work stage part of the board inspection apparatus illustrated in FIG. 1. FIG. 3 is a conceptual view illustrating an optical path of an optical module of the board inspection apparatus illustrated in FIG. 1.

Referring to FIGS. 1 to 3, a board inspection apparatus 100 according to an exemplary embodiment of the present invention includes a worktable 110, a work stage work stage part 120, an optical module 130 and an optical module moving part 140.

The worktable 110 is a table prepared for performing inspection of a board.

The work stage part 120 is installed over the worktable 110 to support a board 10 corresponding to a target of inspection.

The work stage part 120 includes at least two work stages disposed in parallel. For example, the work stage part 120, as shown in FIG. 1, includes a first work stage 122 and a second work stage 124.

The first work stage 122 and the second work stage 124 may receive the board 10 independently, and an inspection for each board 10 may be independently performed at the first work stage 122 and the second work stage 124.

The first work stage 122 and the second work stage 124 may receive the board 10 corresponding to a target of inspection from an apparatus 200 adjacent to a first side. In addition, the first work stage 122 and the second work stage 124 may transfer the board 10 to an apparatus 300 adjacent to a second side opposite to the first side. In FIG. 2, a direction, in which the board is transferred, is referenced to a first direction D1, and thick arrows represent a transfer flow of the board 10.

In an exemplary embodiment, the apparatus 200 adjacent to the first side may include a screen printer for forming solder onto the board 10, and the apparatus 300 adjacent to the second side may include a mounter mounting an electronic element onto the board 10. For example, after the board inspection apparatus 100 receives the board 10 on which solder is formed by the screen printer, the board inspection apparatus 100 inspects whether solder formed on the board 10 is good or bad. In case that the inspection result is good, the board inspection apparatus 100 transfers the board 10 to the mounter, and the mounter mounts an electronic element onto the board 10.

Since the board inspection apparatus 100 includes a plurality of work stages and performs inspection of the board 10 independently for each work stage, time required for inspecting a plurality of boards 10 may be greatly reduced. For example, while one board 10 for inspection is received and inspected at the first work stage 122, another board 10 is received in the second work stage 124 in advance. Then, when the inspection for the one board 10 is completed and transferred to the apparatus 300 adjacent to the second side, inspection for the another board 10 received in the second work stage 124 may be performed. Thus, time for transferring the board 10 may be reduced.

The first work stage 122 and the second work stage 124 may be integrally formed with each other, and alternatively, may be separately formed from each other. In the first work stage 122 and the second work stage 124, the board 10 may be aligned in a second direction D2 substantially perpendicular to the first direction D1 according to the size of the board 10.

The work stage part 120 includes a target moving instrument 126 and a rotating belt 128.

The target moving instrument 126 may move the board 10 transferred to the first and second work stages 122 and 124 to a measurement location in the first direction D1. After the inspection for the board 10 is completed, the target moving instrument 126 transfers the board 10 to the apparatus 300 adjacent to the second side in the first direction D1.

In an exemplary embodiment, the target moving instrument 126 may include a driving motor 126a and a rotating shaft 126b. The driving motor 126a rotates the rotating shaft 126b.

The rotating belt 128 rotates according to rotation of the rotating shaft 126b, and a roller (not shown) that transfers a rotation force of the rotating shaft 126b to the rotating belt 128 may be formed between the rotating belt 128 and the rotating shaft 126b.

In order to inspect the board 10, the optical module 130 generates light and receives the light that is reflected by the board 10, to capture an image. The optical module 130 includes a projecting part 132, an image capturing part 134 and a first optical path changing part 136.

The projecting part 132 is disposed over the board to project grating pattern light onto the board 10. The projecting part 132 projects grating pattern light for obtaining three dimensional information such as height information, visibility information, etc. onto the board 10, so as to measure a three dimensional shape of a measurement target 20 formed on the board 10.

For example, projecting part 132 includes a light source 132a generating light, a grating element 132b converting the light from the light source 132a into grating pattern light, a grating moving instrument 132c pitch-moving the grating element 132b and a projecting lens 132d projecting the grating pattern light converted by the grating element 132b onto the measurement target 20.

The grating element 132b may be moved using a grating moving instrument 132d such as a piezoelectric (PZT) actuator by $2\pi/n$ per one time and n−1 times in total, for generating phase transition of the grating pattern light. The "n" is a natural number of greater than or equal to 2. A plurality of projecting parts 132 having the above-described structure may be disposed apart from each other by a substantially constant angle along a circumferential direction based on the measurement target 20 so as to increase inspection accuracy.

The image capturing part 134 capture a reflection image by receiving the grating pattern light that is upwardly reflected by the board 10. For example, the image capturing part 134 may employ one of a CCD camera and a CMOS camera, and an imaging lens (not shown) may be installed in the image capturing part 134 to form the reflection image on the camera.

The image capturing part 134 is disposed at a side portion of the projecting part 132. In order to secure a space, which become small due to the work stages disposed in parallel, the optical module moving part 140, which is describe later, is installed over the optical module 130, not installed at a side portion of the optical module 130 as a conventional structure. In addition, in order not to deteriorate stability and precision of the optical module 130 due to the optical module moving part 140 installed over the optical module 130, the image capturing part 134 is disposed at the side portion of the projecting part 132, not installed at an upper location substantially perpendicular to the board 10 as a conventional structure. In case that the image capturing part 134 is installed at an upper location substantially perpendicular to the board 10 as a conventional structure, a distance between the optical module 130 and the optical module moving part 140 is increased, thereby deteriorating stability and precision of the optical module 130.

In an exemplary embodiment, the image capturing part 134 may be disposed at a first side portion of the projecting part 132 corresponding to the second direction D2. In FIG. 3, the image capturing part 134 is disposed at the right side of the projecting part 132. Alternatively, the image capturing part 134 may be disposed at the left side of the projecting part 132.

The first optical path changing part 136 changes a path of the grating pattern light upwardly reflected by the board 10 and guiding the grating pattern light to the image capturing part 134 so that the grating pattern light is downwardly incident into the image capturing part 134.

In an exemplary embodiment, the first optical path changing part 136 includes a first mirror 136a and a second mirror 136b.

The first mirror 136a horizontally reflects the grating pattern light that is upwardly reflected by the board 10 toward the side portion of the projecting part 132 at which the image capturing part 134 is located. In other words, the first mirror 136a reflects the grating pattern light that is upwardly reflected by the board 10 to a right direction and provides the reflected grating pattern light to the second mirror 136b.

The second mirror 136b downwardly reflects the grating pattern light that is horizontally reflected by the first mirror 136a toward the image capturing part 134. In other words, the second mirror 136b downwardly reflects the grating pattern light that is reflected to the right direction by the first mirror 136a and provides the reflected grating pattern light to the image capturing part 134 disposed at the side portion of the projecting part 132.

The optical module moving part 140 is disposed over the optical module 130 and coupled to the optical module 130 to move the optical module 130.

In an exemplary embodiment, the optical module moving part 140 includes a first moving guide 142 to move the optical module 130 in the first direction D1 and a second moving guide 144 to move the optical module 130 in the second direction D2. The second moving guide 144 may be supported by guide supports 146 installed at both sides of the worktable 110 corresponding to the second direction D2.

The optical module moving part 140 is not installed at the side portion of the optical module 130 over the worktable 110, but disposed over the optical module 130 and coupled to the optical module 130, to thereby secure a space, which become small due to the work stages disposed in parallel.

The projecting part 132 of the optical module 130, as shown in FIG. 3, may be slantly disposed to project the grating pattern light onto the board 10. However, alternatively, the grating pattern light may be set to be slant by changing a projection path of the grating pattern light.

Figure 4:
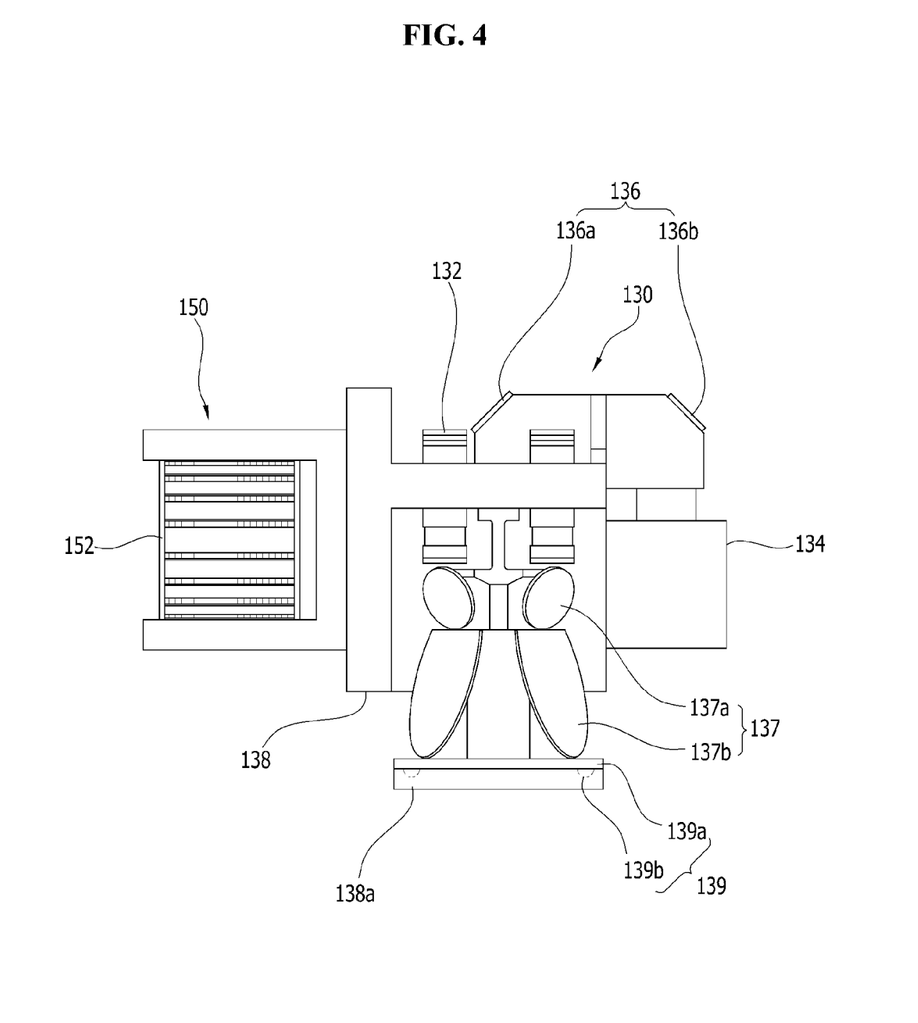
FIG. 4 is a front view illustrating an exemplary embodiment of an optical module of the board inspection apparatus illustrated in FIG. 1.
Figure 5:
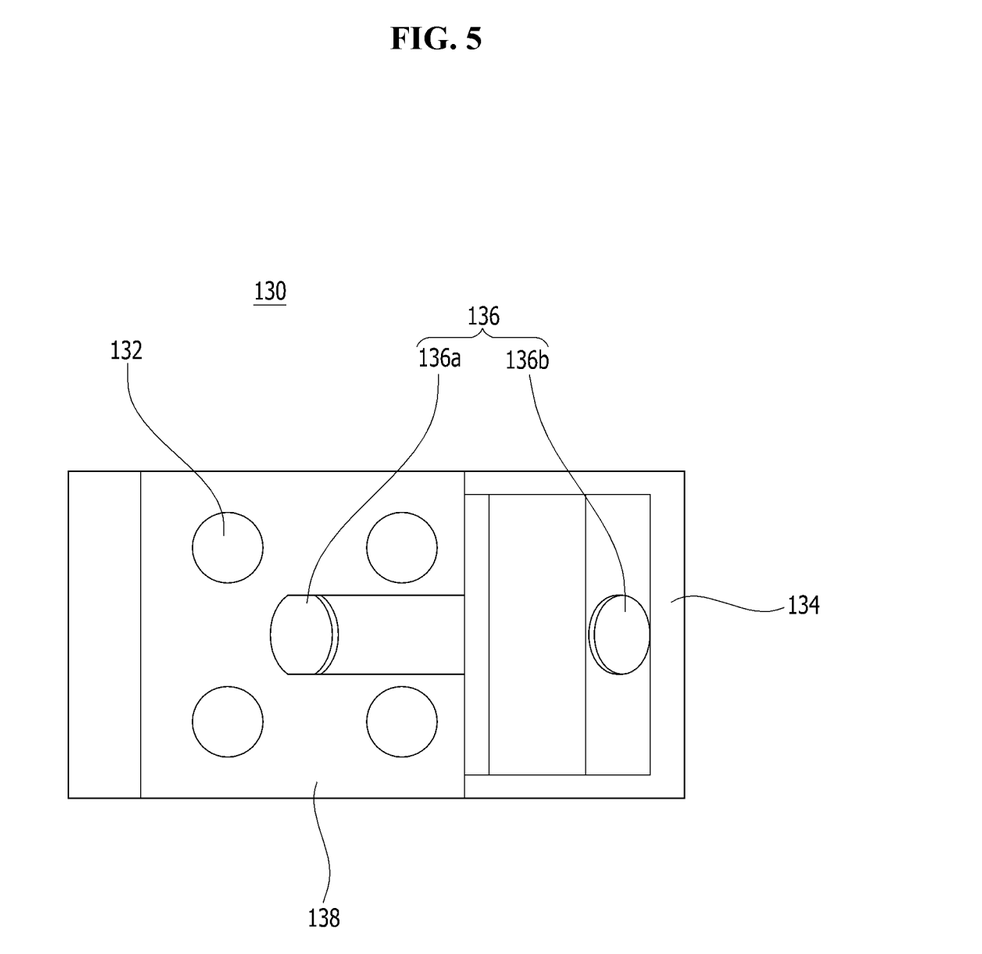
FIG. 5 is a plan view illustrating the optical module of the board inspection apparatus illustrated in FIG. 4.

FIG. 4 is a front view illustrating an exemplary embodiment of an optical module of the board inspection apparatus illustrated in FIG. 1. FIG. 5 is a plan view illustrating the optical module of the board inspection apparatus illustrated in FIG. 4.

Referring to FIGS. 4 and 5, the projecting part 132 may be disposed substantially perpendicular to the board 10. Thus, a space that the projecting part 132 occupies may be reduced, to thereby more efficiently use a workspace.

The optical module 130 may further include a second optical path changing part 137 changing an optical path so that the grating pattern light generated from the projecting part 132 is slantly incident onto the board 10.

In an exemplary embodiment, the second optical path changing part 137 may include a third mirror 137a and a fourth mirror 137b. The third mirror 137a reflects the grating pattern light that is downwardly incident onto the third mirror 137a in a direction substantially perpendicular to the projecting part 132 toward the fourth mirror 137b. The fourth mirror 137b reflects the grating pattern light provided from the third mirror 137b toward the board 10.

For example, the optical module 130 may include 2m projecting parts 132 ('m' is a natural number), and the 2m projecting parts 132 are spaced at a regular interval on a circumference that is substantially parallel with the board 10 when viewed in a plan view. In FIG. 4, the optical module 130 includes four projecting parts 132. In this case, the third mirror 137a is disposed under each of the projecting parts 132, and the fourth mirror 137b is disposed under the third mirror 137a. The third mirror 137a reflects the grating pattern light that is downwardly incident onto the third mirror 137a in a direction substantially perpendicular to the projecting part 132 toward the fourth mirror 137b disposed under and facing the projecting part 132, and the fourth mirror 137b reflects the grating pattern light provided from the third mirror 137a toward the board 10.

Thus, the projecting parts 132 may be substantially perpendicular to the board 10 and a space that the projecting parts 132 occupies may be reduced, to thereby secure a space, which become small due to the work stages disposed in parallel.

The grating element (not shown) corresponding to each of the 2m projecting parts 132 may be moved by one grating moving instrument (not shown). In other words, in case that the projecting parts 132 are disposed substantially perpendicular to the board 10, the projecting parts 132 are parallelly disposed, which is different from in FIG. 3, and thus the grating element corresponding to at least two projecting parts 132 may be moved by using one grating moving instrument.

The projecting part 132, the image capturing part 134, the first optical path changing part 136, and the second optical path changing part 137 may be integrally formed with a body 138. In addition, a light installation part 138a may be disposed under and integrally formed with the body 138. The light installation part 138a may have, for example, a circular shape or quadrangular ring shape. In FIGS. 4 and 5, although reference numerals 136a, 136b, 137a and 137b, strictly speaking, refer to mirror fixing portions fixing the first, second, third and fourth mirrors to the body 138, respectively, the reference numerals are used to refer to the first, second, third and fourth mirrors for convenience.

The optical module 130 may further include an illuminating part 139. The illuminating part 139 may provide light for initial alignment of the board 10, setting an inspection area, etc., and may provide color light for acquiring two dimensional image of the measurement target 20.

In an exemplary embodiment, the illuminating part 139 includes a driving board 139a disposed on an upper face of the light installation part 138a, and a light source 139b disposed on a lower face of the driving board 139a. The driving board 139a corresponds to a printed circuit board (PCB), and drives the light source 139b. The light source 139b provides light to the board 10. For example, the illuminating part 139 may include a fluorescent lamp generating white light, or include at least one of a red light-emitting diode (LED), a green LED and a blue LED that generate red light, green light and blue light, respectively.

The illuminating part 139 provides light for initial alignment, setting an inspection area, etc., or color light for acquiring two dimensional image, which is different from the projecting part 132 that projects grating pattern light for acquiring three dimensional information of the measurement target 20 formed on the board 10. The illuminating part 139 may be integrally formed with the optical module 130 due to the above described structural feature of the board inspection apparatus 100, which is different from the conventional structure.

The third mirror 137a and the fourth mirror 137b may be fixed to the body 138 by a mirror fixing portion. The illuminating part 139 may be disposed under and coupled to the mirror fixing portion to provide light to the board 10.

The board inspection apparatus 100 may further include a cable guiding part 150 that guides various cables employed in the board inspection apparatus 100.

In an exemplary embodiment, the cable guiding part 150 may be disposed at a second side portion opposite to the first side portion of the projecting part 132 at which the image capturing part 134 is disposed. In FIG. 4, the cable guiding part 150 is disposed at the left side of the projecting part 132. Alternatively, in case that the image capturing part 134 is disposed at the left side of the projecting part 132, the cable guiding part 150 may be disposed at the right side of the projecting part 132.

The cable guiding part 150 may include a cable chain 152, and the cable chain 152 helps the cables guided by the cable guiding part 150 to be smoothly moved, not twisted, according as the optical module 130 and the cable guiding part 150 are moved by the optical module moving part 140.

As described above, the board inspection apparatus includes a plurality of work stages, and performs a board inspection independently for each work stage, to thereby greatly reduce time required for inspecting a board. In addition, an optical module moving part for moving an optical module including projecting parts is disposed over the optical module, and an image capturing part receiving grating pattern light generated from the projecting part is disposed at a side portion of the projecting part, to secure a space, which become small due to installing the work stages.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An inspection apparatus comprising:
    a work stage part moving a board to a measurement location and supporting the board;
    an optical module comprising:
        a projecting part disposed over the board to project grating pattern light to the board,
        an image capturing part disposed at a side portion of the projecting part to receive the grating pattern light upwardly reflected by the board and capture a reflection image; and
        a first optical path changing part changing a path of the grating pattern light upwardly reflected by the board and guiding the grating pattern light to the image capturing part so that the grating pattern light is downwardly incident into the image capturing part; and
    an optical module moving part disposed over the optical module and coupled to the optical module to move the optical module,
    wherein the projecting part is disposed substantially perpendicular to the board, and
    the optical module further comprises a second optical path changing part changing an optical path so that the grating pattern light from the projecting part is slantly incident onto the board,
    wherein the optical module comprises 2m projecting parts ('m' is a natural number), and the 2m projecting parts are spaced at a regular interval on a circumference that is substantially parallel with the board when viewed in a plan view,
    wherein the second optical path changing part comprises a third mirror disposed under each of the projecting parts and a fourth mirror disposed under the third mirror, and
    wherein the third mirror reflecting the grating pattern light that is downwardly incident onto the third mirror in a direction substantially perpendicular to the projecting part toward the fourth mirror disposed under and facing the projecting part, and the fourth mirror reflecting the grating pattern light provided from the third mirror toward the board.

2. The inspection apparatus of claim 1, wherein the work stage part comprising a target moving instrument moving the board to the measurement location,
    wherein the target moving instrument moving the board in a first direction, and the optical module moving part moving the optical module in a second direction substantially perpendicular to the first direction, and
    wherein the image capturing part disposed at a first side portion of the projecting part corresponding to the second direction.

3. The inspection apparatus of claim 2, further comprising a cable guiding part disposed at a second side portion opposite to the first side portion of the projecting part at which the image capturing part is disposed.

4. The inspection apparatus of claim 3, wherein the optical module moving part is disposed over and coupled to the cable guiding part.

5. The inspection apparatus of claim 1, wherein the first optical path changing part comprises a first mirror horizontally reflecting the grating pattern light that is upwardly reflected by the board toward the side portion of the projecting part at which the image capturing part is located.

6. The inspection apparatus of claim 5, wherein the first optical path changing part further comprises a second minor downwardly reflecting the grating pattern light that is horizontally reflected by the first mirror toward the image capturing part.

7. The inspection apparatus of claim 1, wherein each of the 2m projecting parts comprises a light source generating light and a grating element converting the light from the light source into grating pattern light, and the grating element corresponding to each of the 2m projecting parts is moved by one grating moving instrument.

8. The inspection apparatus of claim 1, wherein the optical module further comprises an illuminating part integrally coupled to the projecting part, the image capturing part and the first optical path changing part and disposed under a body of the optical module to provide light to the board.

9. An inspection apparatus comprising:
   a projecting part projecting grating pattern light to a board;
   an image capturing part receiving the grating pattern light reflected by the board and capturing a reflection image;
   an optical path changing part comprising at least one mirror changing an optical path so that the grating pattern light from the projecting part is slantly incident onto the board; and
   an illuminating part disposed under the mirror to provide light to the board,
   wherein the inspection apparatus comprises 2m projecting parts ('m' is a natural number), each of which is disposed substantially perpendicular to the board, and the 2m projecting parts are spaced at a regular interval on a circumference that is substantially parallel with the board when viewed in a plan view,
   wherein the optical path changing part comprises a first mirror disposed under each of the projecting parts and a second mirror disposed under the first mirror, and
   wherein the first mirror reflecting the rating pattern light that is downwardly incident onto the first mirror in a direction substantially perpendicular to the projecting part toward the second mirror disposed under and facing the projecting part, and the second mirror reflecting the grating pattern light provided from the first mirror toward the board.

10. The inspection apparatus of claim 9, further comprising:
    a work stage part receiving the board from an adjacent apparatus and moving the board to a measurement location, the work stage part comprising at least two work stages disposed in parallel to support the board; and
    an optical module moving part disposed over the projecting part and the image capturing part and coupled to the projecting part and the image capturing part to move the projecting part and the image capturing part.

* * * * *